United States Patent
Nakhat et al.

(10) Patent No.: US 9,192,596 B2
(45) Date of Patent: *Nov. 24, 2015

(54) SELF-EMULSIFYING PHARMACEUTICAL COMPOSITIONS OF RHEIN OR DIACEREIN

(71) Applicant: WOCKHARDT RESEARCH CENTRE, Aurangabad (IN)

(72) Inventors: Premchand Nakhat, Yavatmal (IN); Prashant Mandaogade, Amravati (IN); Girish Kumar Jain, Delhi (IN); Munish Talwar, Panchkula (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/636,499

(22) Filed: Mar. 3, 2015

(65) Prior Publication Data

US 2015/0164851 A1  Jun. 18, 2015

Related U.S. Application Data

(63) Continuation of application No. 12/680,335, filed as application No. PCT/IB2008/053946 on Sep. 27, 2008, now Pat. No. 8,999,381.

(30) Foreign Application Priority Data

Sep. 27, 2007  (IN) .......................... 1895/MUM/2007
Mar. 24, 2008  (IN) ............................ 576/MUM/2008
May 26, 2008  (IN) .......................... 1115/MUM/2008

(51) Int. Cl.
| | |
|---|---|
| *A61K 9/48* | (2006.01) |
| *A61K 9/64* | (2006.01) |
| *A61K 31/235* | (2006.01) |
| *A61K 9/107* | (2006.01) |
| *A61K 31/222* | (2006.01) |
| *A61K 47/44* | (2006.01) |

(52) U.S. Cl.
CPC ............. *A61K 31/235* (2013.01); *A61K 9/1075* (2013.01); *A61K 9/4825* (2013.01); *A61K 9/4858* (2013.01); *A61K 31/222* (2013.01); *A61K 47/44* (2013.01)

(58) Field of Classification Search
None
See application file for complete search history.

(56) References Cited

U.S. PATENT DOCUMENTS 5,952,383 A    9/1999   Metziger et al.

FOREIGN PATENT DOCUMENTS

EP    0598337 A2    5/1994

*Primary Examiner* — Susan Tran
(74) *Attorney, Agent, or Firm* — Bio Intellectual Property Services LLC (Bio IPS); O. (Sam) Zaghmout

(57) ABSTRACT

The invention relates to self emulsifying drug delivery system based compositions of rhein or diacerein, or salts or esters or prodrugs thereof which are bioequivalent to a 50 mg diacerein formulation marketed under the trade name Art 50®. The compositions exhibit no variability in fed and fasted state conditions. The compositions also result in significant reduction in side effects such as, soft stools effects as compared to Art 50®. The invention also relates to methods for preparing such compositions.

6 Claims, No Drawings

SELF-EMULSIFYING PHARMACEUTICAL COMPOSITIONS OF RHEIN OR DIACEREIN

CROSS-REFERENCE TO RELATED APPLICATIONS

This application is a continuation of U.S. application Ser. No. 12/680,335, filed Jun. 24, 2010, which entered the National Phase of Serial No. PCT/IB2008/053946, Filed Sep. 27, 2008, which claims the benefit of Indian patent applications 1115/MUM/2008, filed May 26, 2008; 576/MUM/2008, filed Mar. 24, 2008; 1895/MUM/2007, filed Sep. 27, 2007. The entire disclosure of these prior applications are hereby incorporated by reference.

FIELD OF THE INVENTION

The invention relates to self emulsifying drug delivery system based compositions of rhein or diacerein, or salts or esters or prodrugs thereof which are bioequivalent to a 50 mg diacerein formulation marketed under the trade name Art 50®. The compositions exhibit no variability in fed and fasted state conditions. The compositions also result in significant reduction in side effects such as, soft stools effects as compared to Art 50®. The invention also relates to methods for preparing such compositions.

BACKGROUND OF THE INVENTION

Chemically, rhein is 9,10-dihydro-4,5-dihydroxy-9,10-dioxo-2-anthracene carboxylic acid having a structure of Formula I and diacerein is 4,5-bis(acetyloxy) 9,10-dihydro-4,5-dihydroxy-9,10-dioxo-2-anthracenecarboxylic acid having a structure of Formula II. Diacerein is widely used in the treatment of osteoarthritis and has a unique mode of action that differentiates it from non-steroidal anti-inflammatory drugs (NSAIDs) and other conventional forms of drug therapy.

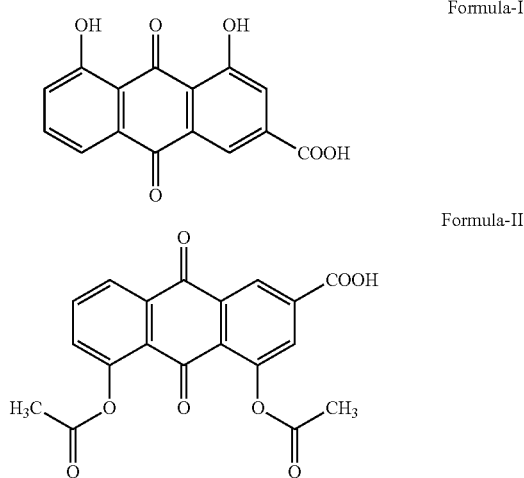

Diacerein is practically insoluble in solvents such as water, alcohols, acetone, dichloromethane and chloroform, which are generally used in pharmaceutical preparations. Although diacerein can be administered by oral route but it cannot be completely absorbed by the digestive tract, and this incomplete absorption may result in undesirable side effects such as, soft stools.

In order to overcome these problems, various derivatives, pharmaceutical compositions and specific galenic forms have been proposed in the literature. For example, European patent, EP 243,968 discloses a potassium salt of diacerein, which is water-soluble and can be used in the preparation of compositions for parenteral administration.

European Patent No EP904060 discloses pharmaceutical compositions of rhein or diacerein, wherein rhein or diacerein is co-micronized with sodium lauryl sulfate.

European Patent Nos. EP263083; 264989 and 446753 disclose controlled release or delayed release compositions like multiplicity of pellets coated with drug and coating membrane or granules of drug coated with polymers or loading polymeric particles of water swellable cross-linked polymer with drug.

U.S. Pat. Nos. 5,225,192 and 5,569,469 describe different poorly soluble medicaments supported on polymeric particles of water swellable cross-linked polymer with drug.

U.S. Pat. No. 5,952,383 and European Patent No. EP 862423B1 provide pharmaceutical compositions of diacerein, rhein and their salts along with liquid support systems like oils, suspending agents, homogenizing agents and other excipients.

It is known that when 50 mg diacerein formulation currently marketed under the trade name Art 50® is given orally in fasted conditions, due to fast gastric emptying, most of the diacerein remains unabsorbed and unabsorbed diacerein gets converted into rhein before reaching colon. At the colonic site, the rhein degrades to rhein-9-anthrone which causes significant soft stool effect. This soft stool effect is observed in about 50% of the patients after first few doses of Art 50®. In fact, about 30-40% soft stool effect is expected due to inherent pharmacokinetic property of diacerein, i.e diacerein undergoes enterohepatic circulation, wherein rhein gets conjugated in liver to form rhein-glucuronide, which on reaching colon gets converted to rhein-9-anthrone and hence causes soft stool effect.

On the other hand, when Art 50® is given in fed conditions, the gastric emptying is delayed in the presence of food. The longer residence time in upper part of the gastrointestinal tract accompanied with gastric fluids results in increased absorption of diacerein. This increase in absorption is up to 25% leading to comparatively less amount of unabsorbed diacerein to reach colon and hence reduction in soft stools. However, this reduction in soft stools is not significant. It was also observed that when the diacerein formulation described in EP 904060 comprising co-micronized diacerein with sodium lauryl sulfate is given, it results in only about 18% reduction in soft stools, which is not significant. This reduction in soft stools is not due to dose reduction but it is related to increased absorption of the diacerein leading to lesser amount of unabsorbed diacerein reaching colon. The diacerein formulation described in EP 904060 also exhibits drastic variation in both fed and fasted conditions. So, prior art formulations are discriminatory with respect to both fast and fed conditions. Additionally, prior art formulations are also eclipsed with undesirable soft stool effect.

Due to soft stool effect, prior art formulations (Art 50® and Art 40) are initially given once a day for about two months, so that the patient's gastrointestinal tract gets acclimatized to the side effect of diacerein. After that, the dosage regimen is scheduled for twice a day for both Art 50® and Art 40. Although, this adjustment of the dosage regimen improves patient's compliance to some extent, but there is no reduction in side effects. There still exists a need to develop new formulations or compositions which are likely to achieve a higher rate and extent of absorption of diacerein leading to improved bioavailability and at the same time shows significant reduction in side effects such as, soft stools.

In spite of the attempts in the prior art, described above, the inventors are not aware of successful attempts to improve the absorption of diacerein and significant reduction in soft stools. As described below, the inventors have surprisingly found that compositions of the invention result in a higher rate and extent of absorption from the gastrointestinal tract and significant reduction (at least 25%) in soft stools. The inventors also have surprisingly found that the compositions can be given with or without food without affecting the rate and extent of absorption. The inventors have further noticed that there is no need to co-micronize diacerein with any surfactant to get a formulation, which is bioequivalent to the commercially available diacerein 50 mg solid oral dosage form (Art 50®).

Thus, the compositions of the invention, overcome all the commonly encountered problems exemplified in the prior art. When the compositions of the invention are given orally, diacerein gets completely absorbed in upper part of intestine and there remains no unabsorbed diacerein reaching colon, resulting in a significant reduction in soft stools effect from about 60-70%. Furthermore, the compositions of the invention are bioequivalent to 50 mg diacerein formulation currently marketed under the trade name Art 50® showing no variability whether administered in fed or fasted state conditions.

SUMMARY OF THE INVENTION

In one general aspect there is provided a self-emulsifying drug delivery system comprising rhein or diacerein, or salts or esters or prodrugs thereof in one or more pharmaceutically acceptable vehicles.

In another general aspect there is provided a pharmaceutical composition comprising from about 20 mg to about 45 mg of rhein or diacerein, or salts or esters or prodrugs thereof, wherein the composition exhibits no significant difference in one or both of the rate and the extent of absorption of the rhein or diacerein as compared to a 50 mg diacerein formulation marketed under the trade name Art 50®, and wherein the composition is a self emulsifying drug delivery system comprising one or more pharmaceutically acceptable vehicles.

The compositions can be taken with or without food.

Embodiments of the pharmaceutical compositions may include one or more of the following features. The pharmaceutical composition may further include one or more pharmaceutically acceptable excipients. For example, the pharmaceutically acceptable excipients may include one or more of fillers, binders, lubricants, sweeteners, glidants, disintegrants, and the like.

In another general aspect there is provided a process for preparing a pharmaceutical composition comprising self-emulsifying drug delivery system of rhein or diacerein, or salts or esters or prodrugs thereof, the process comprising mixing rhein or diacerein, or salts or esters or prodrugs thereof with one or more suitable emulsifiers and/or oils, optionally with pharmaceutically acceptable excipients and converting the mixture into a suitable dosage form.

In another general aspect there is provided a pharmaceutical composition comprising supersaturable self-emulsifying drug delivery system of rhein or diacerein, or salts or esters, or prodrugs thereof in one or more pharmaceutically acceptable vehicles, optionally with one or more pharmaceutically acceptable excipients.

Embodiments of the pharmaceutical composition may include one or more of the following features. The pharmaceutical composition may further include one or more pharmaceutically acceptable polymers.

In another general aspect there is provided a process for preparing a pharmaceutical composition of rhein or diacerein, or salts or esters or prodrugs thereof, the process comprising mixing rhein or diacerein, or salts or esters or prodrugs thereof with one or more suitable emulsifiers and/or oils, optionally with pharmaceutically acceptable polymers and converting the mixture into a suitable dosage form.

Embodiments of the pharmaceutical composition may include one or more of the following features. The pharmaceutical composition may further include one or more pharmaceutically acceptable excipients. For example, the pharmaceutically acceptable excipients may include one or more of fillers, binders, lubricants, sweeteners, glidants, disintegrants, and the like.

The pharmaceutical compositions may be administered to mammals orally and can be present in a liquid or semi-solid form and can be further filled into hard gelatin capsules, soft gelatin capsules, or hydroxypropylmethyl cellulose (HPMC) capsules. The composition may spontaneously form an emulsion on contact with an aqueous environment, for example in the gastrointestinal tract.

The details of one or more embodiments of the inventions are set forth in the description below. Other features, objects and advantages of the inventions will be apparent from the description and claims.

DETAILED DESCRIPTION OF THE INVENTION

The inventors have discovered that when diacerein is formulated in a pharmaceutically acceptable vehicle which includes oils and/or emulsifiers, it forms an emulsion on contact with an aqueous environment i.e a self-emulsifying drug delivery system, it results in a significant increase in the solubility of diacerein and percent drug release of diacerein as compared to Art 50®. The Art 50® releases about 14% of diacerein in 60 minutes, whereas the pharmaceutical composition of the invention releases more than 85% of diacerein in 30 minutes. This leads to increased bioavailability. The increased bioavailability further leads to a significant reduction in side effects i.e. soft stools. The administration of the composition to a human subject in a fasted state is bioequivalent to the administration of the composition to a subject in fed state in particular, as defined by $C_{max}$, $T_{max}$ and AUG guidelines given by the US Food and Drug Administration (US FDA) and European Medicines Agency (EMEA).

Although self-emulsifying drug delivery system is a known technique, but it is highly difficult to predict for which drugs it will work. There are various other factors which vary from drug to drug and influence its bioavailability like pKa, solubility profile both in oil and water, and stability aspects in different media. Non-availability of many products in the market based on this technique is indicative of the unpredictability and the selection of a drug with this technique.

The present inventors have observed that using the self-emulsifying drug delivery system (SEDDS) technology with other known water insoluble drugs like irbesartan, aripiprazole, entacapone, does not result in any significant increase in the solubility or percent release of these poorly soluble drugs.

The assays conducted by the inventors have unexpectedly demonstrated that diacerein can be efficiently formulated by using SEDDS technology, even though the diacerein has an altogether different pharmacokinetic (absorption only from upper part of the intestine, entero-hepatic circulation, soft stool problem) and physico-chemical profile (typical pKa of 4.5, instability under acidic and alkaline conditions).

Further, the inventors have discovered that a high surfactant level typically present in the self-emulsifying drug delivery system leads to gastrointestinal side effects as well as a reduction in the free drug concentration and thus a reduced rate of intestinal absorption. The inventors have now developed a supersaturable self-emulsifying drug delivery system (S-SEDDS) in an attempt to reduce the side effects caused by the surfactant and achieve a rapid absorption of poorly soluble drugs. The S-SEDDS compositions contain a reduced surfactant level as compared to conventional SEDDS system, hence leading to reduced gastrointestinal side effects. The supersaturable self-emulsifying drug delivery system includes pharmaceutically acceptable polymers in pharmaceutically acceptable vehicle comprising oil and/or emulsifiers, which forms an emulsion on contact with an aqueous environment. The polymers prevent precipitation of the drug by generating and maintaining a supersaturated state in vivo. The system generates a supersaturated solution of the drug when the composition is released from an appropriate dosage form into an aqueous medium. The Art 50® releases about 13% of diacerein in 120 minutes, whereas the pharmaceutical composition of the invention releases more than 60% of diacerein in 120 minutes. This leads to increased bioavailability. The increased bioavailability further leads to reduction in side effects i.e. soft stools.

Suitable emulsifiers which can be used include one or more of polyoxyethylene glycerol esters of fatty acids, such as Tagats; polooxylated castor oil, ethylene glycol esters, such as glycol stearate and distearate; propylene glycol esters, such as propylene glycol myristate; glyceryl esters of fatty acids, such as glyceryl stearates and monostearates; sorbitan esters, such as spans and tweens; polyglyceryl esters, such as polyglyceryl 4-oleate; fatty alcohol ethoxylates, such as Brij type emulsifiers; ethoxylated propoxylated block copolymers, such as poloxamers; polyethylene glycol esters of fatty acids, such as Labrafils, Labrafacs, and Labrasols; cremophores; glycerol monocaprylate/caprate, such as Campmul CM 10; Gelucire, Capryol, Captex, Acconon, transcutol, triacetin, and the like.

In particular, a mixture of high HLB surfactant like tweens and a low HLB surfactant like polyethylene glycol esters of fatty acids, such as Labrafils, Labrafacs, and Labrasols can be used. The tweens may be present at a concentration range of about 5% to about 50% w/w, for example from about 10% to about 40% w/w. Labrafacs, Labrasils or Labrasols may be present at a concentration range of about 5% to about 70% w/w, for example from about 7% to about 45% w/w.

Suitable oils which may be used include one or more of Neobee oil; Miglyol derivatives (fractionated coconut oil), soy oil, almond oil, olive oil, peanut oil, other fatty acid esters of glycerols, medium chain triglycerides, and the like.

The pharmaceutically acceptable polymers include one or more of cellulosic polymers or its derivatives including hydroxypropylmethyl cellulose, hydroxy methylcellulose, hydroxy ethyl cellulose, methyl cellulose, hydroxypropyl cellulose, sodium carboxymethyl cellulose, arboxymethylcellulose, polyacrylate/polyalcohol copolymers, gums, polyacrylate/polyacrylamide copolymers, polyvinyl alcohol polymers, acrylic/methacrylic copolymers, carboxyvinyl polymers, galactomannans, polyanhydrides, polyamino acids, polysaccharides, or the derivatives thereof.

In one embodiment, the pharmaceutical composition of the invention may be prepared by mixing rhein or diacerein, or salts or esters or prodrugs thereof with one or more suitable emulsifiers and/or oils, optionally with pharmaceutically acceptable excipients and converting the mixture into a suitable dosage form.

In another embodiment, the pharmaceutical composition of the invention may be prepared by mixing diacerein or salts thereof with one or more suitable emulsifiers and/or oils, optionally with other pharmaceutically acceptable polymers and converting the mixture into a suitable dosage form.

The pharmaceutical compositions of the invention may further include one or more pharmaceutically acceptable excipients selected from the group of fillers, lubricants, sweeteners, colors, disintegrants, surfactants and glidants.

The "pharmaceutical composition" of the invention as used herein, is meant for oral administration to mammals and can be present in the form of a liquid or semi-solid form, which may be further, filled into hard gelatin capsules, soft gelatin capsules, or hydroxypropylmethyl cellulose (HPMC) capsules.

The rhein or diacerein or salts or esters or prodrugs thereof may be present in the form of a powder, granules, pellets, beads, microtablets, minitablets and crystals.

"Bioequivalency" is established by a 90% Confidence Interval (CI) of between 0.80 and 1.25 for both $C_{max}$ and AUC under USFDA regulatory guidelines, or a 90% CI for AUC of between 0.80 to 1.25 and a 90% CI for $C_{max}$ of between 0.70 to 1.43 under the European regulatory guidelines (EMEA).

The term "confidence interval" as used herein refers to the plain meaning known to one of ordinary skill in the art. The confidence interval refers to a statistical range with a specified probability that a given parameter lies within the range.

The term "covariance" as used herein refers to the plain meaning known to one of ordinary skill in the art. It is a statistical measure of the variance of two random variables that are observed or measured in the same mean time period. This measure is equal to the product of the deviations of corresponding values of the two variables from their respective means.

The bioequivalence studies were carried out between Art 50® (reference) and compositions of the invention (test) both in fed state and fasted state. The study was monitored in terms of Cmax, AUC, Tmax achieved with the test products and the reference product (Art 50®).

The compositions of the invention exhibits pharmacokinetic profile characterized by $C_{max}$ of about 3.15 to 6.0 μg/ml, $T_{max}$ of about 2.4 to 5.0 h, $AUC_{0-t}$ of about 16.4 to 40 μg·h/ml, $AUC_\phi$ of about 16.7 to 40 μg·h/ml.

At 90% confidence interval; area under the concentration time curve ($AUC_{0-t}$ and/or $AUC_\phi$) and maximum plasma concentration (Cmax) values of composition of the invention lies between 0.70 and 1.70 as compared to that obtained by a 50 mg diacerein formulation marketed under the trade name Art 50®.

The advantages of the compositions of the invention, include, but are not limited to: (1) smaller solid dosage form size; (2) smaller doses of drug required to obtain the same pharmacological effect; (3) increased bioavailability; (4) substantially similar pharmacokinetic profiles of the rhein or diacerein, compositions when administered in the fed versus the fasted state; (5) bioequivalency of the diacerein compositions when administered in the fed versus the fasted state.

The pharmaceutical composition of the invention may include one or more of other auxiliary agents known in the art like antioxidants, colorants, flavoring agents, preservatives, and the like.

The invention is further illustrated by the following examples which are provided merely to be exemplary of the invention and do not limit the scope of the invention. Certain modifications and equivalents will be apparent to those skilled in the art and are intended to be included within the scope of the invention.

Example 1

TABLE 1

| S.N. | Ingredients | % w/w |
|---|---|---|
| 1 | Diacerein | 11.26 |
| 2 | Labrafil | 7.15 |
| 3 | Labrasol | 38.5 |
| 4 | Tween 80 | 40 |

Procedure: Diacerein was mixed with labrafil, labrasol and tween 80 for few minutes. The mixture thus obtained was sonicated for few minutes and filled into hard gelatin capsules. A gelatin band was applied to the filled hard gelatin capsules.

TABLE 2

| | Dissolution Data | |
|---|---|---|
| Time (min) | % Drug released (Art 50 ®) | % Drug released (Example-1) |
| 5 | 3 | 43 |
| 10 | 4 | 61 |
| 15 | 5 | 73 |
| 20 | 7 | 78 |
| 30 | 9 | 85 |
| 45 | 11 | 90 |
| 60 | 14 | 92 |

Table 2 provides the dissolution data for diacerein capsules prepared as per the formula given in Table 1. For determination of drug release rate, USP Type 2 Apparatus (rpm 75) was used wherein 1000 ml of pH 5.7 Tampon phosphate buffer at 37° C.±0.5° C. was used as a medium.

Example 2

TABLE 3

| S.N. | Ingredients | % w/w |
|---|---|---|
| 1 | Diacerein | 9.50 |
| 2 | Labrafac | 19.2 |
| 3 | Labrasol | 37.8 |
| 4 | Tween 80 | 38 |

Procedure: Diacerein was mixed with labrafac, labrasol and tween 80 for few minutes. The mixture thus obtained was sonicated for few minutes and filled into hard gelatin capsules. A gelatin band was applied to the filled hard gelatin capsules.

TABLE 4

| | Dissolution data | |
|---|---|---|
| Time (min) | % Drug released (Art 50 ®) | % Drug released (Example-2) |
| 5 | 3 | 39 |
| 10 | 4 | 64 |
| 15 | 5 | 75 |
| 20 | 7 | 80 |
| 30 | 9 | 87 |
| 45 | 11 | 92 |
| 60 | 14 | 97 |

Table 4 provides the dissolution data for diacerein capsules prepared as per the formula given in Table 3. For determination of drug release rate, USP Type 2 Apparatus (rpm 75) was used wherein 1000 ml of pH 5.7 Tampon phosphate buffer at 37° C.±0.5° C. was used as a medium.

Example 3

TABLE 5

| S. No. | Ingredients | % w/w |
|---|---|---|
| 1 | Diacerein | 11.90 |
| 2 | Triacetin | 20.0 |
| 3 | Labrasol | 38.3 |
| 4 | Tween 80 | 38.0 |

Procedure: Diacerein was mixed with triacetin, labrasol and tween 80 for few minutes. The mixture thus obtained was sonicated for few minutes and filled into hard gelatin capsules. A gelatin band was applied to the filled hard gelatin capsules.

TABLE 6

| | Dissolution data | |
|---|---|---|
| Time (min) | % Drug released (Art 50 ®) | % Drug released (Example-3) |
| 5 | 3 | 48 |
| 10 | 4 | 63 |
| 15 | 5 | 74 |
| 30 | 7 | 83 |
| 45 | 9 | 87 |
| 60 | 11 | 90 |

Table 6 provides the dissolution data for diacerein capsules prepared as per the formula given in Table 5. For determination of drug release rate, USP Type 2 Apparatus (rpm 75) was used wherein 1000 ml of pH 5.7 Tampon phosphate buffer at 37° C.±0.5° C. was used as a medium.

Example 4

TABLE 7

| S. No. | Ingredients | % w/w |
|---|---|---|
| 1 | Diacerein | 12.56 |
| 2 | Capmul | 10.0 |
| 3 | Acconon | 49.7 |
| 4 | Tween 80 | 30.0 |

Procedure: Diacerein was mixed with capmul, acconon and tween 80 for few minutes. The mixture thus obtained was sonicated for few minutes and filled into hard gelatin capsules. A gelatin band was applied to the filled hard gelatin capsules.

TABLE 8

Dissolution data

| Time (min) | % Drug released (Art 50 ®) | % Drug released (Example-4) |
|---|---|---|
| 5 | 3 | 36 |
| 10 | 4 | 55 |
| 15 | 5 | 68 |
| 30 | 7 | 79 |
| 45 | 9 | 85 |
| 60 | 11 | 89 |

Table 8 provides the dissolution data for diacerein capsules prepared as per the formula given in Table 7. For determination of drug release rate, USP Type 2 Apparatus (rpm 75) was used wherein 1000 ml of pH 5.7 Tampon phosphate buffer at 37° C.±0.5° C. was used as a medium.

Example 5

TABLE 9

| S. No. | Ingredients | % w/w |
|---|---|---|
| 1 | Diacerein | 15.54 |
| 2 | Labrafac | 11.7 |
| 3 | Labrasol | 45.0 |
| 4 | Acconon | 23.5 |
| 5 | Tween 80 | 12 |

Procedure: Diacerein was mixed with labrafac, labrasol, acconon and tween 80 for few minutes. The mixture thus obtained was sonicated for few minutes and filled into hard gelatin capsules. A gelatin band was applied to the filled hard gelatin capsules.

TABLE 10

Dissolution data

| Time (min) | % Drug released (Art 50 ®) | % Drug released (Example-5) |
|---|---|---|
| 5 | 3 | 33 |
| 10 | 4 | 56 |
| 15 | 5 | 67 |
| 30 | 7 | 81 |
| 45 | 9 | 86 |
| 60 | 11 | 88 |

Table 10 provides the dissolution data for diacerein capsules prepared as per the formula given in Table 9. For determination of drug release rate, USP Type 2 Apparatus (rpm 75) was used wherein 1000 ml of pH 5.7 Tampon phosphate buffer at 37° C.±0.5° C. was used as a medium.

Example 6

TABLE 11

| S.N. | Ingredients | % w/w |
|---|---|---|
| 1 | Diacerein | 10-90 |
| 2 | Labrafil | 1-70 |
| 3 | Labrasol | 10-90 |
| 4 | Cremophor | 5-70 |
| 5 | Methocel | 2-50 |

Procedure: Diacerein was mixed with labrafil, labrasol, cremophor and methocel to form a mixture. The mixture was sonicated and filled into hard gelatin capsules. A gelatin band was applied to the filled hard gelatin capsules.

TABLE 12

Dissolution data

| Time (min) | % Drug released (Art 50 ®) | % Drug released (Example-6) |
|---|---|---|
| 15 | 2 | 39 |
| 30 | 6 | 50 |
| 45 | 8 | 56 |
| 60 | 10 | 58 |
| 90 | 11 | 61 |
| 120 | 13 | 62 |

Table 12 provides the dissolution data for diacerein capsules prepared as per the formula given in Table 11. For determination of drug release rate, USP Type 2 Apparatus (rpm 75) was used wherein 1000 ml of pH 5.7 Tampon phosphate buffer at 37° C.±0.5° C. was used as a medium with sinker.

Example 7

TABLE 13

| S.N. | Ingredients | % w/w |
|---|---|---|
| 1 | Diacerein | 10-90 |
| 2 | Labrafil | 1-70 |
| 3 | Labrasol | 10-90 |
| 4 | Cremophor | 5-70 |
| 5 | Gelucire | 5-60 |
| 6 | HPC | 2-50 |

Procedure: Diacerein was mixed with labrafil, labrasol, cremophor, Gelucire and HPC to form mixture. The mixture was sonicated and filled into hard gelatin capsules. A gelatin band was applied to the filled hard gelatin capsules.

TABLE 14

Dissolution data

| Time (min) | % Drug released (Art 50 ®) | % Drug released (Example-7) |
|---|---|---|
| 15 | 2 | 24 |
| 30 | 6 | 44 |
| 45 | 8 | 55 |
| 60 | 10 | 63 |
| 90 | 11 | 71 |
| 120 | 13 | 76 |

Table 14 provides the dissolution data for diacerein capsules prepared as per the formula given in Table 13. For determination of drug release rate, USP Type 2 Apparatus (rpm 75) was used wherein 1000 ml of pH 5.7 Tampon phosphate buffer at 37° C.±0.5° C. was used as a medium with sinker.

Example 8

TABLE 15

| S.N. | Ingredients | % w/w |
|---|---|---|
| 1 | Diacerein | 10-90 |
| 2 | Labrafil | 1-70 |
| 3 | Labrasol | 10-90 |
| 4 | Cremophor | 5-70 |
| 5 | Gelucire | 5-60 |
| 6 | HPC | 2-50 |

Procedure: Diacerein was mixed with labrafil, labrasol, cremophor, Gelucire and HPC to form a mixture. The mixture was sonicated for and filled into hard gelatin capsules. A gelatin band was applied to the filled hard gelatin capsules.

TABLE 16

Dissolution data

| Time (min) | % Drug released (Art 50 ®) | % Drug released (Example-8) |
|---|---|---|
| 15 | 2 | 28 |
| 30 | 6 | 51 |
| 45 | 8 | 65 |
| 60 | 10 | 73 |
| 90 | 11 | 81 |
| 120 | 13 | 84 |

Table 16 provides the dissolution data for diacerein capsules prepared as per the formula given in Table 15. For determination of drug release rate, USP Type 2 Apparatus (rpm 75) was used wherein 1000 ml of pH 5.7 Tampon phosphate buffer at 37° C.±0.5° C. was used as a medium with sinker.

Example 9

TABLE 17

| S. No. | Ingredients | % w/w |
|---|---|---|
| 1 | Diacerein | 10-90 |
| 2 | Labrafil | 1-70 |
| 3 | Labrasol | 10-90 |
| 4 | Cremophor | 5-70 |
| 5 | Gelucire | 5-60 |
| 6 | HPC | 2-50 |

Procedure: Diacerein was mixed with labrafil, labrasol, cremophor, Gelucire and HPC to form a mixture. The mixture was sonicated and filled into hard gelatin capsules. A gelatin band was applied to the filled hard gelatin capsules.

TABLE 18

Dissolution data

| Time (min) | % Drug released (Art 50 ®) | % Drug released (Example-9) |
|---|---|---|
| 15 | 2 | 14 |
| 30 | 6 | 34 |
| 45 | 8 | 50 |
| 60 | 10 | 62 |
| 90 | 11 | 78 |
| 120 | 13 | 85 |

Table 18 provides the dissolution data for diacerein capsules prepared as per the formula given in Table 17. For determination of drug release rate, USP Type 2 Apparatus (rpm 75) was used wherein 1000 ml of pH 5.7 Tampon phosphate buffer at 37° C.±0.5° C. was used as a medium with sinker.

Example 10

TABLE 19

| S.N. | Ingredients | % w/w |
|---|---|---|
| 1 | Diacerein | 10-90 |
| 2 | Labrafil | 1-70 |
| 3 | Labrasol | 10-90 |
| 4 | Cremophor | 5-70 |
| 5 | Gelucire | 5-60 |
| 6 | HPC | 2-50 |

Procedure: Diacerein was mixed with labrafil, labrasol, cremophor, Gelucire and HPC to form a mixture. The mixture was sonicated for few minutes and filled into hard gelatin capsules. A gelatin band was applied to the filled hard gelatin capsules.

TABLE 20

Dissolution data

| Time (min) | % drug released (Art 50 ®) | % drug released (Example-10) |
|---|---|---|
| 15 | 2 | 39 |
| 30 | 6 | 71 |
| 45 | 8 | 87 |
| 60 | 10 | 96 |
| 90 | 11 | 100 |
| 120 | 13 | 100 |

Table 20 provides the dissolution data for diacerein capsules prepared as per the formula given in Table 19. For determination of drug release rate, USP Type 2 Apparatus (rpm 75) was used wherein 1000 ml of pH 5.7 Tampon phosphate buffer at 37° C.±0.5° C. was used as a medium with sinker.

TABLE 21

Bioequivalence data of the composition of the invention against Art 50 ® with respect to pharmacokinetic parameters

| S. No | Pharmacokinetic parameters | Art 50 ® | Composition of the invention |
|---|---|---|---|
| 1 | $C_{max}$ (µg/ml) | 3.058 | 5.35 |
| 2 | $T_{max}$ (h) | 5.39 | 1.25 |
| 3 | $AUC_{0-t}$ (µgh/ml) | 22.688 | 27.149 |
| 4 | $AUC_{\phi}$ (µgh/ml) | 22.816 | 27.332 |

TABLE 22

Bioequivalence data with respect to Test (Composition of the invention) to reference Art 50 ® Ratios (T/R ratios) at 90% Confidence Interval (C.I.)

| S. No | Pharmacokinetic parameters | Ratio | 90% C.I. Lower | 90% C.I. Upper | % CV |
|---|---|---|---|---|---|
| 1 | $C_{max}$ (µg/ml) | 121.94 | 91.33 | 162.82 | 28.15 |
| 2 | $AUC_{0-t}$ (µgh/ml) | 105.69 | 79.73 | 140.10 | 27.42 |
| 3 | $AUC_{\phi}$ (µgh/ml) | 105.79 | 79.75 | 140.33 | 27.49 |

While the invention has been described in terms of its specific embodiments, certain modifications and equivalents will be apparent to those skilled in the art and are intended to be included within the scope of the invention.

The invention claimed is:

1. A pharmaceutical composition comprising about 10-90% w/w of diacerein, about 1-70% w/w of labrafil, about 10-90% w/w of polyoxyethylene glycerol esters of fatty acid, about 5-70% w/w/of PEG 40 hydrogenated castor oil, about 2-50% of methylcellulose, wherein the composition exhibits a dissolution profile such that at least 60% of diacerein is released within 120 minutes, wherein the release rate is measured in Apparatus 2 USP, Dissolution, paddle, 75 rpm) using 1000 ml of pH 5.7 Tampon phosphate buffer at 37° C.±0.5° C.

2. The composition of claim 1, wherein the pharmaceutical composition further comprises one or more pharmaceutically acceptable vehicle.

3. The composition of claim 2, wherein the pharmaceutically acceptable vehicle is selected from the group consisting of one or more of triglycerides of coconut oil, caprylic triglycerides, soy oil, almond oil, olive oil, peanut oil, other fatty acid esters of glycerols and medium chain triglycerides.

4. The composition of claim 1, wherein the pharmaceutical composition further comprises one or more pharmaceutically acceptable excipients.

5. The composition of claim 4, wherein the pharmaceutically acceptable excipients comprises one or more of fillers, binders, lubricants, sweeteners, glidants, and disintegrants.

6. The composition of claim 1, wherein the composition is further filled into hard gelatin capsules, soft gelatin capsules or hydroxypropylmethyl cellulose capsules.

* * * * *